(12) United States Patent
Nielsen et al.

(10) Patent No.: US 8,071,345 B2
(45) Date of Patent: Dec. 6, 2011

(54) STABILIZED SUBTILISIN COMPOSITION

(75) Inventors: Lone Kierstein Nielsen, Kongens Lyngby (DK); Ole Simonsen, Søborg (DK); Karl Werntoft, Malmö (SE); Niclas Ilestam, Malmö (SE)

(73) Assignee: Novozymes A/S, Bagsvaerd (DK)

( * ) Notice: Subject to any disclaimer, the term of this patent is extended or adjusted under 35 U.S.C. 154(b) by 812 days.

(21) Appl. No.: 11/693,514

(22) Filed: Mar. 29, 2007

(65) Prior Publication Data

US 2007/0232514 A1 Oct. 4, 2007

Related U.S. Application Data

(60) Provisional application No. 60/789,413, filed on Apr. 5, 2006.

(30) Foreign Application Priority Data

Mar. 31, 2006 (DK) ................................ 2006 00460

(51) Int. Cl.
*C12N 9/96* (2006.01)
*C12N 9/50* (2006.01)
*C12N 9/56* (2006.01)
*C11D 3/00* (2006.01)

(52) U.S. Cl. ........ 435/188; 435/183; 435/195; 435/219; 435/222; 510/300; 510/305

(58) Field of Classification Search .................. 435/183, 435/195, 212, 219, 188, 222; 510/300, 325
See application file for complete search history.

(56) References Cited

U.S. PATENT DOCUMENTS

| | | | |
|---|---|---|---|
| 3,293,143 A | 12/1966 | Heinicke | |
| 4,717,662 A | 1/1988 | Montgomery et al. | |
| 5,516,672 A | 5/1996 | Yamasaki et al. | |
| 5,919,313 A | 7/1999 | Asgharian et al. | |
| 6,184,189 B1 | 2/2001 | Asgharian et al. | |
| 7,030,069 B2 * | 4/2006 | Gupta et al. ................... | 510/101 |

FOREIGN PATENT DOCUMENTS

| | | |
|---|---|---|
| DE | 39 41 353 A1 | 7/1990 |
| DE | 3941353 | 7/1990 |
| EP | 0 342 924 A | 11/1989 |
| EP | 0 378 261 B | 7/1990 |
| EP | 0 383 373 A | 8/1990 |
| WO | WO 92/19707 | 11/1992 |
| WO | WO 96/41859 | 12/1996 |
| WO | WO 98/22567 | 5/1998 |

OTHER PUBLICATIONS

Zeller et al. Helv. Chim. Acta (1974) 57: 2406-2420.*
Patil et al. Asian J. Microbiol. Biotech. Env. Sci. (2006) 8(4): 861-862.*
Ajithkumar et al. Soil Biol. Biochem. (1998) 30(8/9): 1053-1059.*
Martinez-Blanco et al. J. Indust. Microbiol. (1994) 13: 144-146.*
Wang et al. Protein J. (2004) 23(5): 303-308.*
Molecular & Cellular Biochemistry 51, 1983, p. 5-32.
Keller et al., Biochem. Biophys. Res. Com. 176, 1991, pp. 401-405.
European Patent Office Search Report dated Mar. 20, 2006.

* cited by examiner

*Primary Examiner* — Susan Hanley
(74) *Attorney, Agent, or Firm* — Michael W. Krenicky

(57) ABSTRACT

The present invention relates to a liquid detergent composition comprising a surfactant, a subtilisin and a protease stabilizer that is 3-chlorobenzoic acid, 4-chlorobenzoic acid, 3-chlorophenylacetic acid, 3,5-dichlorobenzoic acid, 3-(3-chlorophenyl)propionic acid or their corresponding salts. The composition can further comprise a another enzyme that is a lipase, an amylase, a cellulase or mixtures thereof. The stabilizer can be present at a concentration of 0.001 to 20% w/w. The concentration of the subtilisin can be at least 1.5 g/L.

20 Claims, No Drawings

STABILIZED SUBTILISIN COMPOSITION

CROSS-REFERENCE TO RELATED APPLICATIONS

This application claims priority or the benefit under 35 U.S.C. 119 of Danish application no. PA 2006 00460 filed Mar. 31, 2006 and U.S. provisional application No. 60/789,413 filed Apr. 5, 2006, the contents of which are fully incorporated herein by reference.

FIELD OF THE INVENTION

The present invention relates to a liquid composition, comprising an enzyme and an enzyme stabilizer. The invention further relates to the use of said liquid composition.

BACKGROUND OF THE INVENTION

Storage stability problems are well known with liquids containing enzyme(s). Especially in enzyme-containing liquid detergents a major problem, in particular if the detergent contains protease, is that of ensuring enzyme activity over time.

The prior art has dealt extensively with improving the storage stability, for example by adding a protease inhibitor.

Boric acid and boronic acids are known to reversibly inhibit proteolytic enzymes. A discussion of the inhibition of one serine protease, subtilisin, by boronic acid is provided in Molecular & Cellular Biochemistry 51, 1983, pp. 5-32.

Boronic acids have very different capacities as subtilisin inhibitors. Boronic acids containing only alkyl groups such as methyl, butyl or 2-cyclohexylethyl are poor inhibitors with methylboronic acid as the poorest inhibitor, whereas boronic acids bearing aromatic groups such as phenyl, 4-methoxyphenyl or 3,5-dichlorophenyl are good inhibitors with 3,5-dichlorophenylboronic acid as a particularly effective one (see Keller et al, Biochem. Biophys. Res. Com. 176, 1991, pp. 401-405).

It is also claimed that aryl boronic acids which have a substitution at the 3-position relative to boron are unexpectedly good reversible protease inhibitors. Especially, acetamidophenyl boronic acid is claimed to be a superior inhibitor of proteolytic enzymes (see WO 92/19707).

In WO 96/41859 substituted phenyl boronic acids are disclosed as suitable enzyme stabilizers.

It has been found that borates are reprotoxic in animals and therefore there is a demand to find alternatives which can be used to stabilize the enzymes in liquid compositions. In a particular embodiment of the present invention the liquid composition does not comprise borate or boric acid.

In EP 0 378 261 S1 an enzyme stabilization system comprising carboxylic acids for aqueous liquid detergent compositions is disclosed.

SUMMARY OF THE INVENTION

One object of the present invention is to provide a stable liquid composition.

It has surprisingly been found that aryl carboxylic acids have extraordinary good capacities as enzyme stabilizers in liquids, especially of the following formula:

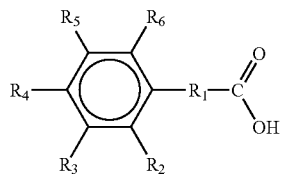

or a salt hereof, wherein $R_1$ is selected from the group consisting of C0, C1, C2, C3, C4, C5 alkyl, substituted C1, C2, C3, C4, C5 alkyl, C1, C2, C3, C4, C5 alkenyl and substituted C1, C2, C3, C4, C5, alkenyl and $R_2$, $R_3$, $R_4$, $R_5$ and $R_6$ is selected from the group consisting of hydrogen, C1, C2, C3, C4, C5, C6 alkyl, substituted C1, C2, C3, C4, C5, C6 alkyl, aryl, substituted aryl, hydroxyl, hydroxyl derivative, amine, C1, C2, C3, C4, C5, C6 alkylated amine, amine derivative, halogen, nitro, thiol, thiol derivative, a aldehyde, acid, acid salt, ester, sulfonate or phosphonate.

The present invention provides thus in a first aspect a liquid composition comprising an enzyme and an enzyme stabilizer of the following formula:

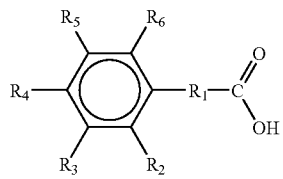

or a salt hereof, wherein $R_1$ is selected from the group consisting of C0-C5 alkyl, substituted C1-C5 alkyl. C1-C5 akenyl and substituted C1-C6 alkenyl and $R_2$, $R_3$, $R_4$, and $R_6$ is selected from the group consisting of hydrogen, C1-C6 alkyl, substituted C1 to C6 alkyl, aryl, substituted aryl, hydroxyl, hydroxyl derivative, amine, C1-C6 alkylated amine, amine derivative, halogen, nitro, thiol, thiol derivative, aldehyde, acid, acid sat, ester, sulfonate or phosphonate.

DETAILED DESCRIPTION OF THE INVENTION

The Stabilizer

The present invention relates to stabilization of enzymes in liquid compositions.

In a particular embodiment the present invention provides a liquid composition comprising an enzyme and an enzyme stabilizer of the following formula:

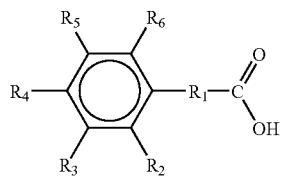

or a salt hereof, wherein $R_1$ is selected from the group consisting of C0-C5 alkyl, substituted C1-C5 alkyl, C1-C5 alkenyl and substituted C1-C6 alkenyl. In a particular embodiment $R_1$ is $CH_2$, $CH_2-CH_2$, $CH_2-CH_2-CH_2$ or $CH_2-CH_2-CH_2-CH_2$. In a most particular embodiment $R_1$ is C0, $CH_2$ or $CH_2-CH_2$, and $R_2$, $R_3$, $R_4$, $R_5$ and/or $R_6$ is selected from the group consisting of hydrogen, C1, C2, C3, C4, C5, C6 alkyl, substituted C1, C2, C3, C4, C5, C6 alkyl, aryl, substituted aryl, hydroxyl, hydroxyl derivative, amine, C1, C2, C3, C4, C5, C6 alkylated amine, amine derivative, halogen, nitro, thiol, thiol derivative, aldehyde, acid, acid salt, ester, sulfonate or phosphonate. In one embodiment $R_2$, $R_3$, $R_4$, $R_5$ and/or $R_6$ is selected from the group consisting of hydrogen, C2, C3, C5, C6 alkyl, substituted C2, C3, C5, C6 alkyl, aryl, substituted aryl, hydroxyl, hydroxyl derivative, amine, C1, C2, C3, C4, C5, C6 alkylated amine, amine derivative, halogen, nitro, thiol, thiol derivative, aldehyde, acid, acid salt, ester, sulfonate or phosphonate.

In a particular embodiment the $R_2$, $R_3$, $R_4$, $R_5$, $R_6$ is $CH_3$—$CH_3CH_2$ and/or $CH_3CH_2CH_2$.

In a particular embodiment the present invention provides a liquid composition comprising an enzyme and an enzyme stabilizer of the formula disclosed above, wherein $R_2$ and $R_6$ are hydrogens.

In another embodiment at least one of the substituents of R2, R3, R4, R5, R6 are selected from the group consisting of C1 to C6 alkyl, substituted C1 to C6 alkyl, aryl, substituted aryl, C1 to C6 alkyl hydroxyl, hydroxyl derivative, amine, C1-C6 alkylated amine, amine derivative, halogen, nitro, thiol, thiol derivative, aldehyde, acid, acid salt, ester, sulfonate and phosphonate.

In a particular embodiment at least one of the substituents of R2, R3, R4, R5, R6 are selected from the group consisting of C2, C3, C5, C6 alkyl, substituted C5, C6 alkyl, aryl, substituted aryl, C2, C3, C5, C6 alkyl hydroxyl, amine, C1-C6 alkylated amine, amine derivative, halogen, nitro, thiol, thiol derivative, aldehyde, acid, acid salt, ester, sulfonate and phosphonate.

In a particular embodiment the stabilizer is selected from the group consisting of benzoic acid, 3-formylbenzoic acid, 4-formylbenzoic acid, 3-nitrobenzoic acid, 4-nitrobenzoic acid, 3,5-dinitrobenzoic acid, 3,4-dinitrobenzoic acid, 3-chlorobenzoic acid, 4-chlorobenzoic acid, 3,5-dichlorobenzoic acid, 3,4-dichlorobenzoic acid, 3-chloromethylbenzoic acid, 4-chloromethyl benzoic acid, 3-aminobenzoic acid, 4-aminobenzoic acid, 3,5-diaminobenzoic acid, 3,4-diaminobenzoic acid, 3-aminomethylbenzoic acid, 4-aminomethylbenzoic acid, 3-hydroxybenzoic acid, 4-hydroxybenzoic acid, 3,5-dihydroxybenzoic acid, 3,4-dihydroxybenzoic acid, 4-hydroxy-3-methoxybenzoic acid (vanillic acid), phenylacetic acid, 3-chlorophenylacetic acid, 4-chlorophenylacetic acid, 3-nitrophenylacetic acid, 4-nitrophenylacetic acid, 3-aminophenylacetic acid, 4-aminophenylacetic acid, 3-phenylpropionic acid, 2-phenylpropionic acid, 3-chlorophenyl-3-propionic acid, 4-chloro-phenyl-3-propionic acid, cinnamic acid and terephthalic acid and their corresponding salts.

In a particular embodiment of the present invention the stabilizer is not Benzoic acid if the pH of the liquid composition is below 7.

It has further been found that aldehydes of the below formula also are particularly well suited as stabilizers in liquid compositions comprising an enzyme. The aldehydes have the following formula:

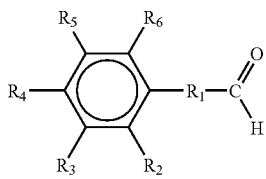

or a salt hereof, wherein $R_1$ is selected from the group consisting of C0-C5 alkyl, substituted C1-C5 alkyl, C1-C5 alkenyl and substituted C1-C6 alkenyl. In a particular embodiment $R_1$ is $CH_2$, $CH_2$—$CH_2$, $CH_2$—$CH_2$—$CH_2$ or $CH_2$—$CH_2$—$CH_2$—$CH_2$. In a most particular embodiment $R_1$ is C0, $CH_2$ or $CH_2$—$CH_2$, and $R_2$, $R_3$, $R_4$, $R_5$ and/or $R_6$ is selected from the group consisting of hydrogen, C1, C2, C3, C4, C5, C6 alkyl, substituted C1, C2, C3, C4, C5, C6 alkyl, aryl, substituted aryl, hydroxyl, hydroxyl derivative, amine, C1, C2, C3, C4, C5, C6 alkylated amine, amine derivative, halogen, nitro, thiol, thiol derivative, aldehyde, acid, acid salt, ester, sulfonate or phosphonate.

In a particular embodiment the $R_2$, $R_3$, $R_4$, $R_5$, $R_6$ is $CH_3$, $CH_3CH_2$ and/or $CH_3CH_2CH_2$.

In a particular embodiment the present invention provides a liquid composition comprising an enzyme and an enzyme stabilizer of the formula disclosed above, wherein $R_2$ and $R_6$ are hydrogens.

In another embodiment at least one of the substituents of R2, R3, R4, R5, R6 are selected from the group consisting of C1 to C6 alkyl, substituted C1 to C6 alkyl, aryl, substituted aryl, C1 to C6 alkyl hydroxyl, hydroxyl derivative, amine, C1-C6 alkylated amine, amine derivative, halogen, nitro, thiol, thiol derivative, aldehyde, acid, acid salt, ester, sulfonate and phosphonate.

In a particular embodiment at least one of the substituents of R2, R3, R4, R5, R6 are selected from the group consisting of C2, C3, C5, C6 alkyl, substituted C5, C6 alkyl, aryl, substituted aryl, C2, C3, C5, C6 alkyl hydroxyl, amine, C1-C6 alkylated amine, amine derivative, halogen, nitro, thiol, thiol derivative, aldehyde, acid, acid salt, ester, sulfonate and phosphonate.

In a particular embodiment the stabilizer is selected from the group consisting of Benzaldehyde, Phenyl acetaldehyde, Phenyl propionaldehyde, 3,5-dichlorobenzaldehyde, 4-formyl-benzaldehyde, 4-carboxybenzaldehyde, 3-chlorobenzaldehyde, 4-chlorobenzaldehyde, 3-(3-chlorophenyl)propionaldehyde, 3-chlorophenylacetaldehyde, 3-(4-chlorophenyl)propion-aldehyde, 4-chlorophenylacetaldehyde, 2-chlorophenylacetaldehyde, 2-chlorobenzaldehyde, 2-aminobenzaldehyde, 3-aminobenzaldehyde, 4-aminobenzaldehyde, 3-bromobenzaldehyde, 3-iodobenzaldehyde, 3-nitrobenzaldehyde, 3-fluorobenzaldehyde, 3-formylbenzaldehyde, 3-(chloromethyl)benzaldehyde, 3,5-dihydroxybenzaldehyde, 4-phenylbutyraldehyde.

In a particular embodiment the enzyme stabilizer is substituted in its 3, 4 and/or 5 position. In a more particular embodiment the enzyme stabilizer is substituted in its 4 position i.e. para-substituted. In a most particular embodiment the enzyme stabilizer is substituted in its 3 and/or 5 positions.

In a particular embodiment of the present invention the liquid composition comprises 0.001-20% w/w of the stabilizer. In a more particular embodiment of the present invention the liquid composition comprises 0.01-15% of the stabilizer. In an even more particular embodiment of the present invention the liquid composition comprises 0.1-10% w/w of the stabilizer. In a most particular embodiment of the present invention the liquid composition comprises 0.5-5% of the stabilizer. In a further particular embodiment of the present invention the liquid composition comprises 1.5 to 5% w/w of the stabilizer.

In a particular embodiment of the present invention the liquid composition comprises 0.05-1000 mM of the stabilizer. In a more particular embodiment of the present invention the liquid composition comprises 0.5-750 mM of the stabilizer. In an even more particular embodiment of the present invention the liquid composition comprises 5-500 mM of the stabilizer. In a most particular embodiment of the present invention the liquid composition comprises 25-250 mM of the stabilizer.

In a particular embodiment the present invention provides a liquid detergent composition comprising a surfactant, an enzyme and an enzyme stabilizer of any of the formulas disclosed above.

It has surprisingly been found that the stabilizer also have a stabilizing effect at pH above 8 such as above 9.

Active Compounds

According to the invention the liquid composition contains at least one enzyme. The enzyme may be any commercially available enzyme, in particular an enzyme selected from the group consisting of proteases, amylases, lipases, cellulases, lyases, oxidoreductases and any mixture thereof. Mixtures of enzymes from the same class (e.g. proteases) are also included.

In a particular embodiment the liquid composition comprises more than 2 different enzymes. According to the invention a liquid composition comprising a protease is preferred. In a particular embodiment a liquid composition comprising two or more enzymes in which the first enzyme is a protease and the second enzyme is selected from the group consisting of amylases, lipases, cellulases, lyases and oxidoreductases is preferred. In a more particular embodiment the second enzyme is a lipase.

It is to be understood that enzyme variants (produced, for example, by recombinant techniques) are included within the meaning of the term "enzyme". Examples of such enzyme variants are disclosed, e.g. in EP 251,446 (Genencor), WO 91/00345 (Novozymes), EP 525,610 (Solvay) and WO 94/02618 (Gist-Brocades NV).

Enzymes can be classified on the basis of the handbook Enzyme Nomenclature from NC-IUBMB, 1992), see also the ENZYME site on the internet located at an address designated www.expasy.ch/enzyme. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase and alpha-galactosidase, in families based on amino acid sequence similarities has been proposed a few years ago. They currently fall into 90 different families: See the CAZy (ModO) internet site (Coutinho, P. M. & Henrissat, B. (1999) Carbohydrate-Active Enzymes server on the internet located at an address designated afmb.cnrs-mrs.fr/~CRAZy/index.html (corresponding papers: Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12; Coutinho, P. M. & Henrissat, B. (1999) The modular structure of cellulases and other carbohydrate-active enzymes: an integrated database approach. In "Genetics, Biochemistry and Ecology of Cellulose Degradation"., K. Ohmiya, K. Hayashi, K. Sakka, Y. Kobayashi, S. Karita and T. Kimura eds., Uni Publishers Co., Tokyo, pp. 15-23).

The liquid composition preferably comprises a protease, such as a serine protease.

Proteases: Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium pro-tease described in WO 89/06270. In a particular embodiment of the present invention the protease is a serine protease. Serine proteases or serine endopeptidases (newer name) are a class of peptidases which are characterised by the presence of a serine residue in the active center of the enzyme.

Serine proteases: A serine protease is an enzyme which catalyzes the hydrolysis of peptide bonds, and in which there is an essential serine residue at the active site (White, Handler and Smith, 1973 "Principles of Biochemistry," Fifth Edition, McGraw-Hill Book Company, NY, pp. 271-272).

The bacterial serine proteases have molecular weights in the 20,000 to 45,000 Daltons range. They are inhibited by diisopropylfluorophosphate. They hydrolyze simple terminal esters and are similar in activity to eukaryotic chymotrypsin, also a serine protease. A more narrow term, alkaline protease, covering a sub group, reflects the high pH optimum of some of the serine proteases, from pH 9.0 to 11.0 (for review, see Priest (1977) Bacteriological Rev. 41 711-753).

Subtilases: A sub-group of the serine proteases tentatively designated subtilases has been proposed by Siezen et al. (1991), Protein Eng., 4 719-737. They are defined by homology analysis of more than 40 amino acid sequences of serine proteases previously referred to as subtilisin-like proteases. A subtilisin was previously defined as a serine protease produced by Gram-positive bacteria or fungi, and according to Siezen et al. now is a subgroup of the subtilases. A wide variety of subtilisins have been identified, and the amino acid sequence of a number of subtilisins have been determined. These include more than six subtilisins from Bacillus strains, namely, subtilisin 168, subtilisin BPN', subtilisin Carlsberg, subtilisin Y, subtilisin amylosacchariticus, and mesentericopeptidase (Kurihara et al. (1972) J. Biol. Chem. 247 5629-5631; Wells et al. (1983) Nucleic Acids Res. 11 7911-7925; Stahl and Ferrari (1984) J. Bacteriol. 159 811-819, Jacobs et al. (1985) Nucl. Acids Res. 13 8913-8926; Nedkov et al. (1985) Biol. Chem. Hoppe-Seyler 366 421-430, Svendsen et al. (1986) FEBS Lett. 196 228-232), one subtilisin from an actinomycetales, thermitase from Thermoactinomyces vulgaris (Meloun et at. (1985) FEBS Lett. 198 195-200), and one fungal subtilisin, proteinase K from Tritrachium album (Jany and Mayer (1985) Biol. Chem. Hoppe-Seyler 366 584-492) for further reference Table I from Siezen et al. has been reproduced below.

Subtilisins are well-characterized physically and chemically. In addition to knowledge of the primary structure (amino acid sequence) of these enzymes, over 50 high resolution X-ray structures of subtilisins have been determined which delineate the binding of substrate, transition state, products, at least three different protease inhibitors, and define the structural consequences for natural variation (Kraut (1977) Ann. Rev. Biochem. 46 331-358).

One subgroup of the subtilases, I-S1, comprises the "classical" subtilisins, such as subtilisin 168, subtilisin BPN', subtilisin Carlsberg (ALCALASE®, Novozymes A/S), and subtilisin DY. A further subgroup of the subtilases I-S2, is recognised by Siezen et al. (supra). Sub-group I-S2 proteases are described as highly alkaline subtilisins and comprise enzymes such as subtilisin PB92 (MAXACAL®, Gist-Brocades NV), subtilisin 309 (SAVINASE®, Novozymes A/S), subtilisin 147 (ESPERASE®, Novozymes A/S), and alkaline elastase YaB.

Random and site-directed mutations of the subtilase gene have both arisen from knowledge of the physical and chemical properties of the enzyme and contributed information relating to subtilase's catalytic activity, substrate specificity, tertiary structure, etc. (Wells et al. (1987) Proc. Natl. Acad. Sci. U.S.A. 84; 1219-1223; Wells et al. (1986) Phil. Trans. R. Soc. Lond. A. 317 415-423; Hwang and Warshel (1987) Biochem. 26 2669-2673, Rao et al., (1987) Nature 328 551-554.

More recent publications covering this area are Carter et al. (1989) Proteins 6 240-248 relating to design of variants that cleave a specific target sequence in a substrate (positions 24 and 64); Graycar et al. (1992) Annals of the New York Academy of Sciences 672 71-79 discussing a number of previously published results; and Takagi (1993) Int. J. Biochem. 25 307-312 also reviewing previous results.

Examples of commercially available proteases (peptidases) include Kannase™, Everlase™, Esperase™, Alcalase™, Neutrase™, Durazym™, Savinase™, Ovozyme™, Pyrase™, Pancreatic Trypsin NOVO (PTN), Bio-Feed™ Pro and Clear-Lens™ Pro (all available from Novozymes A/S, Bagsvaerd, Denmark). Other preferred proteases include those described in WO 01/58275 and WO 01/58276.

Other commercially available proteases include Ronozyme™ Pro, Maxatase™, Maxacal™, Maxapem™, Opticlean™, Propease™, Purafect™ and Purafect Ox™ (available from Genencor International Inc., Gist-Brocades, BASF, or DSM Nutritional Products).

Lipases: Suitable lipases include those of bacterial or fungal origin. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a *Candida* lipase, such as a *C. antarctica* lipase, e.g., the *C. antarctica* lipase A or B described in ER 214 761, a *Pseudomonas* lipase such as a *P. pseudoalcaligenes* and *P. alcaligenes* lipase, e.g., as described in EP 218 272, a *P. cepacia* lipase, e.g., as described in EP 331 376, a *P. stutzeri* lipase, e.g., as disclosed in BP 1,372,034, a *P. fluorescens* lipase, a *Bacillus* lipase, e.g., a *B. subtilis* lipase (Dar-tois et al., (1993), Biochemica et Biophysica acta 1131, 253-260), a *B. stearothermophilus* lipase (JP 64/744992) and a *B. pumilus* lipase (WO 91/16422).

Furthermore, a number of cloned lipases may be useful, including the *Penicillium camenbertii* lipase described by Yamaguchi et al., (1991), Gene 103, 61-67), the *Geotricum candidum* lipase (Schimada, Y. et al., (1989). J. Biochem. 106, 383-388), and various *Rhizopus* lipases such as a *R. delemar* lipase (Hass, M. J. et al., (1991), Gene 109, 117-113), a *R. niveus* lipase (Kugimiya et al., (1992), Biosci. Biotech. Biochem. 56, 716-719) and a *R. oryzae* lipase.

Other types of lipolytic enzymes such as cutinases may also be useful, e.g., a cutinase derived from *Pseudomonas mendocina* as described in WO 88/09367, or a cutinase derived from *Fusarium solani pisi* (e.g. described in WO 90/09446).

Examples of commercially available lipases include Lipex™, Lipoprime™, Lipopan™, Lipolase™, Lipolase™ Ultra, Lipozyme™, Palatase™, Resinase™, Novozym™ 435 and Lecitase™ (all available from Novozymes A/S).

Other commercially available lipases include Lumafast™ (*Pseudomonas mendocina* lipase from Genencor International Inc.), Lipomax™, (*Ps. pseudoalcaligenes* lipase from Gist-Brocades/Genencor Int. Inc.; and *Bacillus* sp. lipase from Solvay enzymes. Further lipases are available from other suppliers such as Lipase R "Amano" (Amano Pharmaceutical Co. Ltd.).

Amylases: Suitable amylases ($\alpha$ and/or $\beta$) include those of bacterial or fungal origin. Chemically or genetically modified mutants are included. Amylases include, for example, a-amylases obtained from a special strain of *B. licheniformis*, described in more detail in British Patent Specification No. 1,296,839. Commercially available amylases are Duramyl™, Termamyl™, Fungamyl™, and BAN™ (available from Novozymes A/S) and Rapidase™ and Maxamyl P™ (available from Gist-Brocades).

Cellulases: Suitable cellulases include those of bacterial or fungal origin. Chemically or genetically modified mutants are included. Suitable cellulases are disclosed in U.S. Pat. No. 4,435,307, which discloses fungal cellulases produced from *Humicola insolens*. Especially suitable cellulases are the cellulases having color care benefits. Examples of such cellulases are cellulases described in European patent application No. 0 495 257.

Oxidoreductases: Any oxidoreductase suitable for use in a liquid composition, e.g., peroxidases or oxidases such as laccases, can be used herein. Suitable peroxidases herein include those of plant, bacterial or fungal origin. Chemically or genetically modified mutants are included. Examples of suitable peroxidases are those derived from a strain of *Coprinus*, e.g., *C. cinerius* or *C. macrorhizus*, or from a strain of *Bacillus*, e.g., *B. pumilus*, particularly peroxidase according to WO 91/05858. Suitable laccases herein include those of bacterial or fungal origin. Chemically or genetically modified mutants are included. Examples of suitable laccases are those obtainable from a strain of *Trametes*, e.g., *T. villosa* or *T. versicolor*, or from a strain of *Coprinus*, e.g., *C. cinereus*, or from a strain of *Myceliophthora*, e.g., *M. thermophila*.

The types of enzymes which may be present in the liquid of the invention include oxidoreductases (EC 1.-.-.-.) transferases (EC 2.-.-.-), hydrolases (EC 3.-.-.-) lyases (EC 4.-.-.-), isomerases (EC 5.-.-.-) and ligases (EC 6.-.-.-).

Preferred oxidoreductases in the context of the invention are peroxidases (EC 1.11.1), laccases (EC 1.10.3.2) and glucose oxidases (EC 1.1.3.4)). An Example of a commercially available oxidoreductase (EC 1.-.-.-) is Gluzyme™ (enzyme available from Novozymes A/S). Further oxidoreductases are available from other suppliers. Preferred transferases are transferases in any of the following sub-classes:

a Transferases transferring one-carbon groups (EC 2.1);
b transferases transferring aldehyde or ketone residues (EC 2.2); acyltransferases (EC 2.3);
c glycosyltransferases (EC 2.4);
d transferases transferring alkyl or aryl groups, other that methyl groups (EC 2.5); and
e transferases transferring nitrogenous groups (EC 2.6).

A most preferred type of transferase in the context of the invention is a transglutaminase (protein-glutamine γ-glutamyltransferase, EC 2.3.2.13).

Further examples of suitable transglutaminases are described in WO 96/06931 (Novozymes A/S).

Preferred hydrolases in the context of the invention are, carboxylic ester hydrolases (EC 3.1.1.-) such as lipases (EC 3.1.1.3); phytases (EC 3.1.3.-), e.g. 3-phytases (EC 3.1.3.8) and 6-phytases (EC 3.1.3.26); glycosidases (EC 3.2, which fail within a group denoted herein as "carbohydrases"), such as α-amylases (EC 3.2.1.1); peptidases (EC 3.4, also known as proteases); and other carbonyl hydrolases. Examples of commercially available phytases include Bio-Feed™, Phytase (Novozymes), Ronozyme™ P (DSM Nutritional Products), Natuphos™ (BASF), Finase™ (AB Enzymes), and the Phyzyme™ product series (Danisco). Other preferred phytases include those described in WO 98/28408, WO 00/43503, and WO 03/066847.

In the present context, the term "carbohydrase" is used to denote not only enzymes capable of breaking down carbohydrate chains (e.g. starches or cellulose) of especially five- and six-membered ring structures (i.e. glycosidases, EC 3.2), but also enzymes capable of isomerizing carbohydrates, e.g. six-membered ring structures such as D-glucose to five-membered ring structures such as D-fructose.

Carbohydrases of relevance include the following (EC numbers in parentheses):

α-amylases (EC 3.2.1.1), β-amylases (EC 3.2.1.2), glucan 1,4-α-glucosidases (EC 3.2.1.3), endo-1,4-beta-glucanase (cellulases, EC 3.2.1.4), endo-1,3(4)-β-glucanases (EC 3.2.1.6), endo-1,4-β-xylanases (EC 3.2.1.8), dextranases (EC 3.2.1.11), chitinases (EC 3.2.1.14), polygalacturonases (EC 3.2.1.15), lysozymes (EC 3.2.1.17), β-glucosidases (EC 3.2.1.21), α-galactosidases (EC 3.2.1.22), β-galactosidases (EC 3.2.1.23), amylo-1,6-glucosidases (EC 3.2.1.33), xylan 1,4-β-xylosidases (EC 3.2.1.37), glucan endo-1,3-β-D-glucosidases (EC 3.2.1.39), α-dextrin endo-1,6-α-glucosidases (EC3.2.1.41), sucrose α-glucosidases (EC 3.2.1.48), glucan endo-1,3-α-glucosidases (EC 3.2.1.59), glucan 1,4-β-glucosidases (EC 3.2.1.74), glucan endo-1,6-β-glucosidases (EC 3.2.1.75), galactanases (EC 3.2.1.89), arabinan endo-1,5-α-L-arabinosidases (EC 3.2.1.99), lactases (EC 3.2.1.108), chitosanases (EC 3.2.1.132) and xylose isomerases (EC 5.3.1.5).

Examples of commercially available carbohydrases include Alpha-Gal™, Bio-Feed™ Alpha, Bio-Feed™ Beta, Bio-Feed™ Plus, Bio-Feed™ Wheat, Bio-Feed™ Z, Novozymes™ 188, Carezyme™, Celluclast™, Cellusoft™, Celluzyme™, Ceremyl™, Citrozym™, Denimax™, Dezyme™, Dextrozyme™, Duramyl™, Energex™, Finizym™, Fungamyl™, Gamanase™, Glucanex™, Lactozym™, Liquezyme™, Maltogenase™, Natalase™, Pentopan™, Pectinex™, Promozyme™, Pulpzyme™, Novamyl™, Termamyl™, AMG™ (Amyloglucosidase Novo), Maltogenase™, Sweetzyme™ and Aquazym™ (all available from Novozymes A/S). Further carbohydrases are available from other suppliers, such as the Roxazyme™ and Ronozyme™ product series (DSM Nutritional Products), the Avizyme™, Porzyme™ and Grindazyme™ product series (Danisco, Finnfeeds), and Natugrain™ (BASF), Purastar™ and Purastar™ OxAm (Genencor).

Other commercially available enzymes include Mannaway™, Pectaway™, Stainzyme™, and Renozyme™.

The Composition

The composition may be any composition, but particularly suitable compositions are cleaning compositions, personal care compositions, textile processing compositions e.g. bleaching, pharmaceutical compositions, leather processing compositions, pulp or paper processing compositions, food and beverage compositions and animal feed compositions.

In a particular embodiment of the present invention the liquid composition is a liquid detergent, e.g. laundry detergent or dishwashing detergent. In a more particular embodiment of the present invention the composition comprises a surfactant.

The invention is further directed to the use of the liquid enzyme additive in liquid detergent composition.

The liquid composition may be a concentrated product to be added to liquid detergents. The amount of enzyme used in the liquid composition is thus very high. In a particular embodiment of the present invention the amount of enzyme present in the liquid composition is at least 1.5 g/L. In a more particular embodiment of the present invention the amount of enzyme is at least 5 g/L. In an even more particular embodiment of the present invention the amount of enzyme present is at least 10 g/L. In a most particular embodiment of the present invention the amount of enzyme present is at least 20 g/L such as even above 25 g/L. In a particular embodiment the amount of enzyme does not exceed 200 g/L. In a more particular embodiment of the present invention the amount of enzyme does not exceed 150 g/L. In a most particular embodiment of the present invention the amount of enzyme present in the liquid composition is less than 100 g/L.

In a particular embodiment of the present invention the liquid composition has a pH of more than 7.5. In a more particular embodiment the pH of the liquid composition is at least 7.7. In a most particular embodiment the pH of the liquid composition is at least 8.0.

In a most particular embodiment of the present invention the liquid composition contain one or more detergent builders. In a particular embodiment of the present invention the liquid composition comprises at least 1% w/w of detergent builders. In a more particular embodiment of the present invention the liquid composition comprises at least 2% w/w of detergent builders. In a most particular embodiment of the present invention the liquid composition comprises at least 5% w/w of detergent builders.

The present invention is further described by the following examples which should not be construed as limiting the scope of the invention.

Detergent Compositions

In a particular embodiment of the present invention the liquid composition is a liquid detergent composition. In a more particular embodiment of the present invention the liquid composition is a liquid detergent composition for dishwashing or for laundry.

The enzyme of the invention may be added to and thus become a component of a detergent composition.

The detergent composition of the invention may for example be formulated as a hand or machine laundry detergent composition including a laundry additive composition suitable for pretreatment of stained fabrics and a rinse added fabric softener composition or be formulated as a detergent composition for use in general household hard surface cleaning operations, or be formulated for hand or machine dishwashing operations.

The detergent composition may comprise one or more enzymes such as a protease, a lipase, a cutinase, an amylase, a carbohydrase, a cellulase, a pectinase, a mannanase, an arabinase, a galactanase, a xylanase, an oxidase, e.g. a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusariunm* protease described in WO 89/06270 and WO 94/25583.

Examples of useful proteases are the variants described in WO 92119729, WO 98/20115, WO 98/20116, and WO 98/34946.

Preferred commercially available protease enzymes include Alcalase™, Savinase™, Primase™, Duralase™, Esperase™, and Kannase™, (Novozymes A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase. e.g., from *P. alcaligenes* or *P. pseudoalcaligenes* (EP 218 272), *P. cepacia* (EP 331 376), *P. stutzeri* (GB 1,372,034), *P. fluoresceins, Pseudomonas* sp. strain SD 705 (WO 95/06720 and WO 96/27002), *P. wiscosinensis* (WO 96/12012), a *Bacillus* lipase, e.g. from *B. subtillis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novozymes A/S).

Amylases: Suitable amylases (α and/or β) include those of bacterial or fungal origin. Chemically modified or protein engineered mutants are included. Amylases include, for example, α-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424.

Commercially available amylases are Duramyl™, Termamyl™, Fungamyl™ and BAN™ (Novozymes A/S), Rapidase™, and Purastar™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusariunm, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes.

A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), polyvinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar, sugar alcohol or lactic acid.

In a particular embodiment of the present invention the liquid composition comprises less than 30% w/v of polyol, such as less than 25% w/v of polyol or even less than 20% w/v of polyol.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

EXAMPLES

Example 1

The inhibition constant $K_I$=[E][I]/[EI] for the inhibition of Savinase was determined using standard methods under the following conditions:
Substrate: Succinyl-Alanine-Alanine-Proline-para-nitro-anilide=SAAPFpNA (Sigma S-7388).
Buffer: 0.1 M phosphate buffer pH 7.5
Temperature: 25° C.
Enzyme concentration in assay≈$1 \times 10^{-8}$ M
The initial rate of substrate hydrolysis was determined with and without inhibitor at nine substrate concentrations in the range of 0.01 mM to 2 mM using an automated spectrophotometer.
The inhibition constant $K_I$ was determined using Sigma Plot 9.0, Enzyme Kinetics Module 1.1

| Inhibitor | $K_i$ |
| --- | --- |
| Benzoic Acid | 22 mM |
| Phenylacetic acid | 10 mM |
| Phenylpropionic acid | 9 mM |
| 3,5-dichorobenzoic acid | 2 mM |
| 4-formylbenzoic acid | 25 mM |
| Terephtalic acid (4-carboxybenzoic acid) | 99 mM |

Example 2

The inhibition constant $K_I$=[E][I]/[EI] for the inhibition of Savinase was determined using standard methods under the following conditions:
Substrate: Succinyl-Alanine-Alanine-Proline-para-nitro-anilide=SAAPFpNA (Sigma S-7388).
Buffer: 0.1 M phosphate buffer pH 7.5
Temperature: 25° C.
Enzyme concentration in assay≈$1 \times 10^{-8}$ M
The initial rate of substrate hydrolysis was determined with and without inhibitor at nine substrate concentrations in the range of 0.01 mM to 2 mM using an automated spectrophotometer.
The inhibition constant $K_I$ was determined using Sigma Plot 9.0, Enzyme Kinetics Module 1.1
Acids:

| Inhibitor | $K_i$ |
| --- | --- |
| 3-chlorobenzoic acid | 4 mM |
| 4-chlorobenzoic acid | 5 mM |
| 3-(3-chlorophenyl)propionic acid | 5 mM |
| 3-chlorophenylacetic acid | 7 mM |
| 3-(4-chlorophenyl)propionic acid | 10 mM |
| 4-chlorophenylacetic acid | 11 mM |
| 2-chlorophenylacetic acid | 11 mM |
| 2-chlorobenzoic acid | 16 mM |
| 2-aminobenzoic acid | 16 mM |
| 3-aminobenzoic acid | 43 mM |
| 4-aminobenzoic acid | 82 mM |
| 3-bromobenzoic acid | 6 mM |
| 3-iodobenzoic acid | 9 mM |
| 3-nitrobenzoic acid | 9 mM |
| 3-fluorobenzoic acid | 17 mM |
| 3-formylbenzoic acid | 27 mM |
| 3-(chloromethyl)benzoic acid | 32 mM |
| 3,5-dihydroxybenzoic acid | 76 mM |
| 3-hydroxybenzoic acid | 29 mM |
| 4-phenylbutyric acid | 19 mM |

Example 3

The inhibition constant $K_I$=[E][I]/[EI] for the inhibition of Savinase was determined using standard methods under the following conditions:
Substrate: Succinyl-Alanine-Alanine-Proline-para-nitro-anilide=SAAPFpNA (Sigma S-7388).
Buffer: 0.1 M phosphate buffer pH 7.5
Temperature: 25° C.
Enzyme concentration in assay≈$1 \times 10^{-8}$ M
The initial rate of substrate hydrolysis was determined with and without inhibitor at nine substrate concentrations in the range of 0.01 mM to 2 mM using an automated spectrophotometer.
The inhibition constant $K_I$ was determined using Sigma Plot 9.0, Enzyme Kinetics Module 1.1
Aldehydes tested:

| Inhibitor | Ki |
| --- | --- |
| 3-hydroxybenzaldehyde | 16 mM |
| 3,4-dihydrozybenzaldehyde | 11 mM |

The invention claimed is:
1. A liquid detergent composition comprising a surfactant, a subtilisin and a protease stabilizer, wherein the protease stabilizer is selected from the group consisting of 3-chlorobenzoic acid, 4-chlorobenzoic acid, 3-chlorophenylacetic acid, 3,5-dichlorobenzoic acid, 3-(3-chlorophenyl)propionic acid, and their corresponding salts.
2. The liquid detergent composition in accordance with claim 1, further comprising a second enzyme comprising amylase, lipase, cellulase, oxidoreductase, and mixtures thereof.
3. The liquid detergent composition according to claim 1, wherein said protease stabilizer is 0.001-20% w/w of the liquid detergent composition.
4. The liquid detergent composition in accordance with claim 1, comprising a second enzyme, wherein the second enzyme is an amylase.
5. The liquid detergent composition in accordance with claim 1, wherein the subtilisin is present in the liquid detergent composition in an amount of at least 1.5 g/L.
6. The liquid detergent composition in accordance with claim 1, wherein the composition has a pH of at least 8.
7. The liquid detergent composition of claim 1, wherein the protease stabilizer is 3-chlorobenzoic acid or a salt thereof.
8. The liquid detergent composition of claim 1, wherein the protease stabilizer is 4-chlorobenzoic acid or a salt thereof.

9. The liquid detergent composition of claim 1, wherein the protease stabilizer is 3-chlorophenylacetic acid or a salt thereof.

10. The liquid detergent composition of claim 1, wherein the protease stabilizer is 3,5-dichlorobenzoic acid or a salt thereof.

11. The liquid detergent composition of claim 1, wherein the protease stabilizer is 3-(3-chlorophenyl)propionic acid or a salt thereof.

12. The liquid detergent composition of claim 1 further comprising an amylase.

13. The liquid detergent composition of claim 1 further comprising a lipase.

14. The liquid detergent composition of claim 1 further comprising a cellulase.

15. The liquid detergent composition of claim 1 further comprising an oxidoreductase.

16. A liquid detergent composition comprising a surfactant, a subtilisin and a protease stabilizer, wherein the protease stabilizer is 3-chlorobenzoic acid or a salt thereof, and wherein said stabilizer is 0.001-20% w/w of the liquid composition.

17. The liquid detergent composition in accordance with claim 16, further comprising a second enzyme comprising amylase, lipase, cellulase, oxidoreductase, and mixtures thereof.

18. A liquid detergent composition comprising a surfactant, a subtilisin and a protease stabilizer, wherein the protease stabilizer is selected from the group consisting of 3-chlorobenzoic acid, 4-chlorobenzoic acid, 3-chlorophenylacetic acid, 3,5-dichlorobenzoic acid, 3-(3-chlorophenyl)propionic acid, and their corresponding salts, wherein the composition has a pH of at least 8, and wherein said stabilizer is 0.001-20% w/w of the liquid composition.

19. The liquid detergent composition of claim 18, wherein the protease stabilizer is 3-chlorobenzoic acid or a salt thereof.

20. The liquid detergent composition in accordance with claim 18, further comprising a second enzyme comprising amylase, lipase, cellulase, oxidoreductase, and mixtures thereof.

* * * * *